(12) United States Patent
Fries et al.

(10) Patent No.: US 8,741,285 B2
(45) Date of Patent: Jun. 3, 2014

(54) METHOD FOR TREATING A PATIENT

(76) Inventors: Dietmar Fries, Innsbruck (AT); Michael Rieger, Zirl (AT)

( * ) Notice: Subject to any disclaimer, the term of this patent is extended or adjusted under 35 U.S.C. 154(b) by 600 days.

(21) Appl. No.: 12/793,992

(22) Filed: Jun. 4, 2010

(65) Prior Publication Data

US 2011/0300122 A1 Dec. 8, 2011

(51) Int. Cl.
*A61K 38/48* (2006.01)
*A61K 35/14* (2006.01)

(52) U.S. Cl.
USPC ........................................ 424/94.64; 530/384

(58) Field of Classification Search
None
See application file for complete search history.

(56) References Cited

FOREIGN PATENT DOCUMENTS

| DE | 19907783 | 8/2000 |
|---|---|---|
| DE | 10307637 | 9/2004 |
| DE | 102004024468 | 12/2005 |
| EP | 1787870 | 5/2007 |
| WO | 03/042004 | 5/2003 |
| WO | 2006/126941 | 11/2006 |

OTHER PUBLICATIONS

Udy et al., "The use of recombinant activated Factor VII in the control of haemorrhage following blunt pelvic trauma", Anaesthesia, 2005, 60, pp. 613-616.*
Williams et al., "First military use of activated Factor VII in an APC-III pelvic fracture", Injury, Int. J. Care Injured (2005), 36, 395-399.*
Golino et al., "Antithrombotic Effects of Recombinant Human, Active Site_Blocked Factor VIIa in a Rabbit Model of Recurrent Arterial Thrombosis", Circ Res. 1998;82:39-46.*
Vick et al., "Recombinant factor VIIa as an adjunct in nonoperative management of solid organ injuries in children", Journal of Pediatric Surgery (2008) 43, 195-199.*

\* cited by examiner

*Primary Examiner* — Suzanne M Noakes
(74) *Attorney, Agent, or Firm* — Dilworth & Barrese, LLP

(57) ABSTRACT

Intra-arterial administering at least one blood coagulation to a bleeding patient is provided, together with a pharmaceutical composition therefor.

24 Claims, 4 Drawing Sheets

METHOD FOR TREATING A PATIENT

BACKGROUND OF THE INVENTION

The invention relates to a method for treating a patient comprising the administration of a blood coagulation factor. The invention further relates to a pharmaceutical composition comprising at least one blood coagulation factor.

It is known in trauma medicine that life-threatening internal bleeding may occur as a consequence of complex pelvic traumata. A complex pelvic trauma involves pelvic fractures complicated by pelvic and extra-pelvic secondary injuries, which is the case at regular intervals. The most common cause of injuries of this kind are accidents involving a massive physical impact of some sort, and therefore most patients are also severely traumatized. Literary sources put the fatality rate associated with complex pelvic injuries as high as 80%. The common cause of death in the early stages is a hemorrhagic shock due to internal bleeding, usually from the Arteria Iliaca, the sacral vein plexus and/or the spongy bone areas of the fractured pelvic ring. Blood may freely flow into the pelvic cavity, since the building up of a counter pressure that would cause a so-called "Own Tamponade" does usually not take place.

Most writers do not recommend exploring a pelvic haematoma with an intact peritoneum. The most important therapeutic concept consists therefore of a primary stabilization of the pelvic fracture in order to attain a compression effect and effectively restrict bleeding from the spongy bone areas. Erythrocyte concentrate (EC) is administered to compensate for the blood loss.

If an increase in the volume of the hematoma is observed during a monographic development check, the most likely reason lies with an arterial injury. Under these circumstances, Own Tamponade has proven ineffective because of the completely ruptured vascular walls. Direct hemostasis is not usually useful because of the time required and the multiple sources of bleeding. The temporary clamping of the aorta is effective, but hardly applicable or to be preferred. Not enough clinical data are available for pelvic slings and pelvic belts.

Catheter embolization is frequently described as an efficient procedure. This procedure involves the selective occlusion of the ruptured vessels by purposely introducing emboli via an arterial catheter by interventional radiology. A localization of the bleeding by angiography is necessary before the procedure. It requires a high degree of skill on the part of the responsible radiologist and even in the hands of an experienced person it requires a very large amount of time to carry out. This constitutes a severe drawback in the emergency treatment. Despite its increasing availability in many clinics, angiography usually takes place five to seventeen hours after admission, according to the literature on the subject. The average requirement of EC is given as 1.2/h, while patients who are being treated with the pelvic clamp or pelvic tamponade require an average EC amount of 2.8/h to 8/h. The angiographic method of haemostasis in patients with unstable pelvic injuries and accompanying circulation instability should therefore be confined to patients with persistent pelvic bleeding whose circulation has been able to be stabilized through adequate volume therapy. Excepted are so-called borderline patients with severe trauma (ISS>20 and additional thorax trauma, multiple trauma with abdominal/pelvic trauma and hemorrhagic shock [initial RR<90 mmHg]; or ISS≥40 without additional thorax injuries, bilateral lung contusions in the primary thorax X-ray) and patients in extremis with acute danger of exsanguination.

SUMMARY OF THE INVENTION

In the light of the above, it is the purpose of the present invention to employ blood coagulation factors in the emergency treatment of patients to stop bleeding.

To solve this problem, a method and a pharmaceutical composition are provided. Preferred embodiments are described in the dependent claims. As such, the invention relates to a method for treating of a bleeding patient which involves the intra-arterial administration of a blood coagulation factor. The invention is further directed to a pharmaceutical composition or medicine comprising at least one coagulation factor suitable for the intra-arterial administration to a patient.

In a preferred embodiment, the method or composition is employed to stop internal bleeding in the patient, in particular internal bleeding due to injuries of arterial blood vessels.

The inventors have surprisingly found out that the intra-arterial administration of blood coagulation factors constitutes a very efficient method of treating internal bleeding due to one or more ruptured arterial vessels and effects a fast, efficient and resistant occlusion of the injured vessels. Massive blood loss following an internal injury can be effectively avoided. The treatment is very simple and can be carried out in less specialized hospitals and other improvized or mobile facilities (mobile treatment units such as ambulances or helicopters, field hospitals, sickbeds), as opposed to for example catheter embolization. The cost to perform a method according to the invention is equivalent to or less than the cost of catheter embolization or other, less efficient methods.

In another preferred embodiment, the blood coagulation factor used for a method or composition in accordance with the invention is Proconvertin (FVII), preferably Activated Proconvertin (FVIIa), and most preferably Recombinant Activated Proconvertin (rFVIIa). Recombinant Activated Proconvertin (rFVIIa) was originally licensed as a method of treating inhibiting antibody haemophilia. rFVIIa works in the presence of a tissue factor: the starting point of the clotting process is the binding and activation of factor VII by the bonding of tissue factor of the sub endothelical cells, whereby thrombin occurs, which in turn activates platelets and factor X. rFVIIa binds in supra-physiological dosage onto the platelets and produces a "thrombine burst" which leads to an extremely stable clot.

According to a further preferred embodiment, the blood coagulation factor is injected at a suitable point in the arterial system, for example at a position which is easily accessible to the trained person involving low time effort and risk. Preferably, the administration takes place in the injured vessel, and more preferably upstream of the injury. Preferred ranges of distance to the injury comprise less than about 30 cm, less than about 25 cm, less than about 20 cm, less than about 15 cm, less than about 10 cm and less than about 5 cm. Proximity to the point of the bleeding is advantageous, but not necessary. The time effort and the demand on the skill of the treating physician or emergency helper is substantially reduced in comparison with methods according to the state of the art.

In one embodiment, the method or composition in accordance with the invention is intended for being employed in a mobile unit. Examples include an ambulance, a helicopter, an aircraft, a boat or ship and similar. In another embodiment, the method or composition is intended for a temporary or improvised unit such as a field hospital, a sickbed and similar facilities. In yet another embodiment, the method or composition is intended for the emergency treatment without the supportive environment of a treating facility.

In a further embodiment, the method or composition is intended for the acute and urgent treatment of patients, such as first aid or treatment in the time before and directly after admission to a medical facility. The invention also comprises the use of the method or composition for the treatment of patients at risk of exsanguination.

In another embodiment, the method or composition according to the invention is intended for the non-surgical treatment of patients, preferably without previous anesthesia.

In one embodiment, the method or composition in accordance with the invention is intended for the emergency treatment of injured soldiers.

In a preferred embodiment of the invention, provision is made that the method involves a one-time only intra-arterial administration. Typically, the bleeding can be stopped by a one-time administration only. Multiple administrations are, however, also covered by the invention.

In a preferred embodiment, the method or composition involves administration in a dosage regimen of between about 50 µg and about 150 µg of the coagulation factor per kilogram body weight. Preferred dosage regimes include the range of between about 75 µg and about 125 µg per kilogram body weight and the range of between about 90 and about 110 µg per kilogram body weight. About 100 µg per kilogram body weight is particularly preferred.

The method or composition according to the invention may be employed in the treatment of bleeding due to injuries following an accident or in the treatment of disease-related bleeding (cancer, . . . ).

In a preferred embodiment, the method or composition is intended for the treatment of pelvic bleeding, for example as a result of complex pelvic traumata. In patients suffering from complex pelvic traumata hemorrhagic shocks are frequent and the bleedings often difficult to stop by methods previously known in the art. In this embodiment, the method or composition is still more preferably directed to the treatment of ruptures of the Arteria Iliaca Communis, the Arteria Iliaca Externa, the Arteria Iliaca Interna, and branches thereof.

In another preferred embodiment, the method or composition is intended for the treatment of bleeding in the shoulder area, in particular the treatment of bleeding due to a rupture of the Arteria Axillaris.

The method or composition according to the invention can be employed in the treatment of humans or animals.

All abovementioned embodiments are comprised alone or in combination by the present invention.

BRIEF DESCRIPTION OF THE DRAWINGS

Further details and advantages of the invention are described in the following Figures and embodiments.

The Figures show.

DESCRIPTION OF THE PREFERRED EMBODIMENTS

EXAMPLE 1

Pig 1 was premedicated with Azaperone 4 mg/kg IM (Stressnil™, Janssen, Vienna, Austria) and Atropine 0.1 mg/kg IM one hour before the start of testing.

Immediately before the start of testing, the pig was anesthetized with Propofol 2 mg/kg iv and Piritramide 30 mg iv (Dipidolor™, Janssen, Vienna, Austria). Anesthesia was maintained during the experiment. Pancuronium 0.2 mg/kg*h iv was continuously administered for muscle relaxation after intubation.

Following the delivery of the intubation and anesthesia, preparation of both Arteriae Femorales and Venae Femorales was performed. The basic fluid requirement (4 mg/kg) was replaced during the entire process by crystalloid (coagulation lactate).

Subsequently, the following invasive catheters were inserted into the vessels:

large bore (large single lumen venous aditus with a length of 15 cm), invasive arterial pressure measurement, and sluice for the insertion of the angiography probe.

Figure 1:
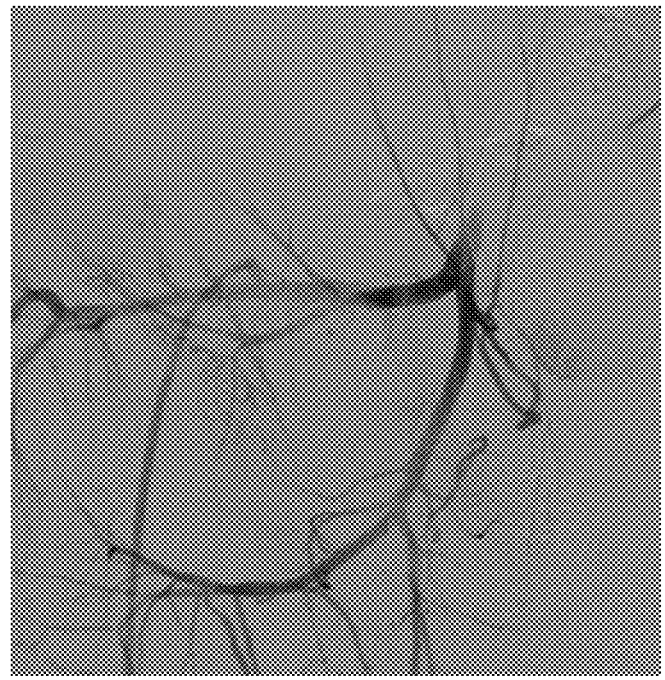
FIG. 1: an angiogram of an intact Arteria Iliaca of a pig.

A DAS of the healthy arteria was recorded and is shown in FIG. 1. (top: A. iliaca communis; left: A. iliaca externa; right: A. iliaca interna).

Figure 2:
FIG. 2: an angiogram of a ruptured Arteria Iliaca of a pig.

Subsequently, the right A. iliaca int. was disrupted using a balloon dilatation. FIG. 2 shows an angiogram immediately after the injury to the A. iliaca interna. The hematoma which was formed can be clearly recognized at the rupture site. The arterial branches downstream of the rupture site are no longer supplied. The A. iliaca externa is also no longer supplied due to the pressure drop. The catheter can be vaguely recognized inside the A. iliaca interna.

After the balloon dilatation the catheter was drawn back from the rupture site by approximately 3 to 5 cm and a dosage of 100 µg/kg rFVIIa (Novo Seven®, NovoNordisk, Denmark) was administered through the catheter intra-arterially upstream of the rupture site.

Any modification of the circulatory system, for example using catecholamine, did not occur.

Figure 3:
FIG. 3: an angiogram of a ruptured Arteria Iliaca of a pig 1 min after intra-arterial treatment with rFVIIa.

The bleeding stopped after only one minute. FIG. 3 shows the angiogram of the injured vascular system one minute after intra-arterial administration of the rFVIIa. The hematoma has blurred and the supply of the surrounding vessels (incl. A. iliaca externa) is reestablished. A clot blocks the A. iliaca interna at the damaged point.

Figure 4:
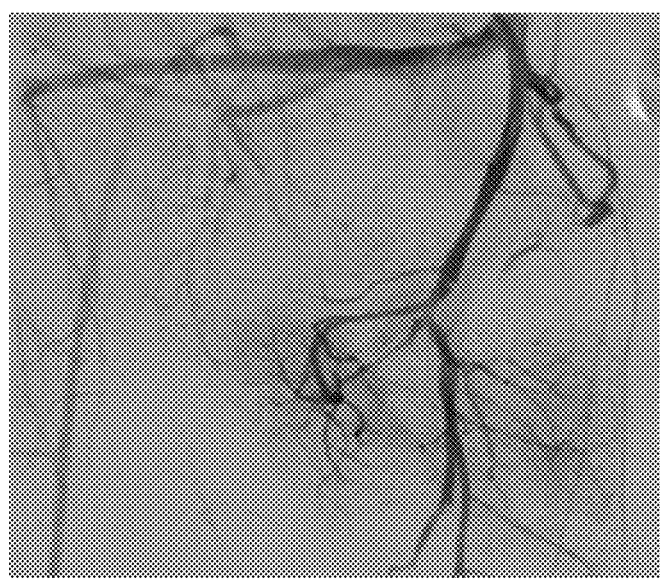
FIG. 4: an angiogram of a ruptured Arteria Iliaca of a pig 5 min after intra-arterial treatment with rFVIIa.

The clot also keeps blocking the damaged point stably after 5 minutes, see FIG. 4.

COMPARATIVE EXAMPLE 1

Pig 2 was treated identically to pig 1.

Instead of rFVIIa, however, saline was injected intra-arterially. The bleeding continued and the pig exsanguinated after 40 minutes.

EXAMPLE 2

Pig 3 was pretreated and anesthetized identically to pig 1.

Figure 5:
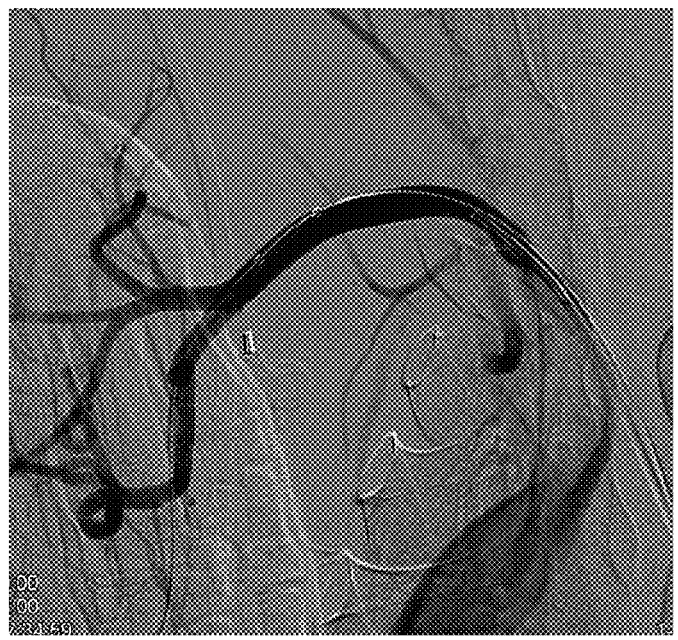
FIG. 5: an angiogram of an intact Arteria Axillaris of a pig.

The invasive catheters (as in Example 1) were inserted into the right Arteria Axillaris. A DAS of the healthy arteria was recorded. The angiogram is shown in FIG. 5.

Figure 6:
FIG. 6: an angiogram of a ruptured Arteria Axillaris of a pig.

Subsequently, the right A. Axillaris was disrupted using a balloon dilatation. FIG. 6 shows an angiogram immediately after the injury to the A. axillaris, with the recognizable formation of a hematoma at the rupture site and a pressure drop. The arterial branches downstream of the rupture site are no longer supplied. The catheter inside the vessel can easily be recognized.

After the balloon dilatation the catheter was drawn back from the rupture site by approximately 5 cm and a single dosage of 100 µg/kg rFVIIa (Novo Seven®, NovoNordisk, Denmark) was administered through the catheter intra-arterially upstream of the rupture site. The bleeding stopped after 3 minutes.

EXAMPLE 3

Pig 4 was pretreated and anesthetized identically to pig 1. The invasive catheters (as in Example 1) were then inserted into the right Arteria Axillaris.

Figure 7:
FIG. 7: an angiogram of a severely ruptured Arteria Axillaris of a pig.

Subsequently, the right A. Axillaris was extensively disrupted using a balloon dilatation. FIG. 7 shows an angiogram immediately after the injury, where a massive hematoma and the absence of blood supply to the vessel can be recognized. The catheter inside the vessel can easily be recognized.

Figure 8:
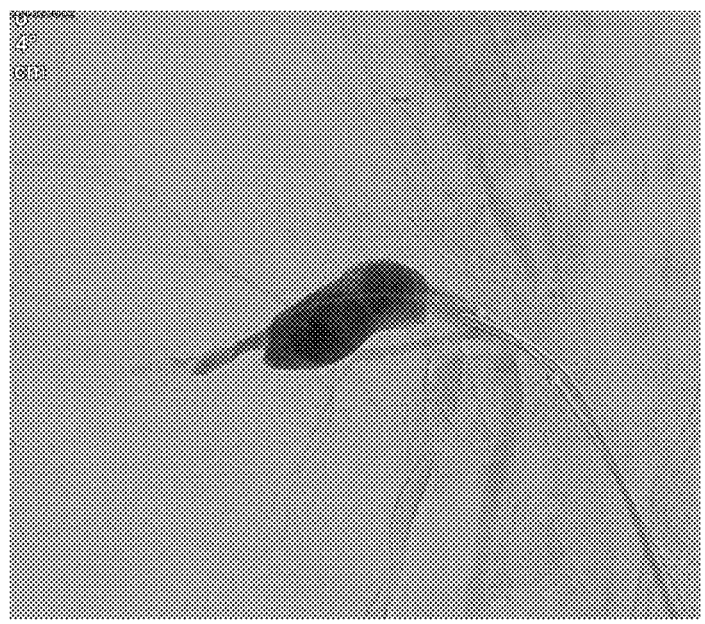
FIG. 8: an angiogram of a severely ruptured Arteria Axillaris of a pig 17 min after intra-arterial treatment with rFVIIa.

After the balloon dilatation the catheter was drawn back from the rupture site by approximately 5 cm and a single dosage of 100 µg/kg rFVIIa (Novo Seven®, NovoNordisk, Denmark) was administered through the catheter intra-arterially upstream of the rupture site. The bleeding stopped after 17 minutes. FIG. 8 shows the respective angiogram 17 minutes after the balloon dilatation. A clot occludes the injury to the vessel and the blood pressure increases. Blood supply is visible from the angiogram.

The study time frame can be summarized as follows:
1. Administration of the anesthetics;
2. Attachment of central venous lines as well as puncturing of both Ae. femorales with attachment of the invasive pressure monitor as well as the introduction of the balloon-tip catheter.
3. Disruption of the A. Iliaca int./A. Axillaris by means of balloon dilatation.
4. Administering of 100 µg/kg body weight rFVIIa or saline through the drawn back catheter.
5. Ending of the test after a maximum of one hour following the balloon dilatation.

It was demonstrated that the intra-arterial administration of the rFVIIa can stop arterial bleeding quickly and efficiently.

The invention claimed is:

1. A method for stopping internal bleeding in a patient in need thereof, comprising intra-arterial administration of a blood coagulation factor, wherein
the internal bleeding results from iniuries to arterial blood vessels,
the method is carried out during emergency treatment,
the intra-arterial administration is carried out under anaiographic control, and
the blood coagulation factor is administered upstream of the injury to the vessel.

2. The method of claim 1, wherein the patient suffers from pelvic injuries.

3. The method of claim 2, wherein the pelvic injury is a complex pelvic trauma.

4. The method of claim 2, wherein the pelvic injuries comprise disrupted vessels selected from the group of the arteria iliaca communis, the arteria iliaca externa, the arteria iliaca interna and branches thereof.

5. The method of claim 1, wherein the blood coagulation factor is proconvertin (FVII).

6. The method of claim 5, wherein the blood coagulation factor is activated proconvertin (FVIIa).

7. The method of claim 6, wherein the blood coagulation factor is recombinant activated proconvertin (rFVIIa).

8. The method of claim 1, wherein the method is intended for a non-surgical treatment.

9. The method of claim 1, wherein the method is intended to be carried out in a mobile treatment facility.

10. The method of claim 1, wherein the administration of the blood coagulation factor is a one-time administration of a single dose of the blood coagulation factor.

11. The method of claim 1, wherein between about 50 and about 150 µg coagulation factor per kg body weight are administered.

12. The method of claim 11, wherein between about 75 and about 125 µg coagulation factor per kg body weight are administered.

13. The method of claim 12, wherein between about 90 and about 110 µg coagulation factor per kg body weight are administered.

14. The method of claim 1, wherein the blood coagulation factor is administered less than about 30 cm. upstream of the injury.

15. The method of claim 14, wherein the blood coagulation factor is administered less than about 20 cm. upstream of the injury.

16. The method of claim 15, wherein the blood coagulation factor is administered less than about 15 cm. upstream of the injury.

17. The method of claim 16, wherein the blood coagulation factor is administered less than about 10 cm. upstream of the injury.

18. The method of claim 17, wherein the blood coagulation factor is administered less than about 5 cm. upstream of the injury.

19. The method of claim 1, wherein the blood coagulation factor is administered to treat ruptures of the Arteria Iliaca Communis, Arteria Iliaca Externa, Arteria Iliaca Interna and branches thereof.

20. The method of claim 1, wherein the blood coagulation factor is intra-arterially administered in the absence of other invasive surgical procedure.

21. The method of claim 1, wherein the blood coagulation factor is intra-arterially administered in the absence of administering anesthesia.

22. The method of claim 1, wherein bleeding stops in less than 17 minutes after administration.

23. The method of claim 22, wherein bleeding stops in less than 3 minutes after administration.

24. The method of claim 23, wherein bleeding stops in less than 1 minute after administration.

* * * * *